(12) United States Patent
Kizaki et al.

(10) Patent No.: US 7,531,329 B2
(45) Date of Patent: May 12, 2009

(54) CARBONYL REDUCTASE, GENE THEREOF AND METHOD OF USING THE SAME

(75) Inventors: Noriyuki Kizaki, Takasago (JP); Tozo Nishiyama, Takasago (JP); Yoshihiko Yasohara, Takasago (JP)

(73) Assignee: Kaneka Corporation, Osaka (JP)

( * ) Notice: Subject to any disclaimer, the term of this patent is extended or adjusted under 35 U.S.C. 154(b) by 6 days.

(21) Appl. No.: 11/730,549

(22) Filed: Apr. 2, 2007

(65) Prior Publication Data

US 2007/0178565 A1 Aug. 2, 2007

Related U.S. Application Data

(62) Division of application No. 10/528,000, filed as application No. PCT/JP03/11957 on Sep. 19, 2003, now Pat. No. 7,220,564.

(30) Foreign Application Priority Data

Sep. 19, 2002 (JP) .............................. 2002-272976

(51) Int. Cl.
C12P 17/04 (2006.01)
C07H 21/04 (2006.01)
C12N 1/20 (2006.01)

(52) U.S. Cl. .................... 435/126; 536/23.2; 435/252.3; 435/252.33; 435/189

(58) Field of Classification Search ........................ None
See application file for complete search history.

(56) References Cited

U.S. PATENT DOCUMENTS

2004/0235124 A1 11/2004 Kawano et al.

FOREIGN PATENT DOCUMENTS

| EP | 0 654 534 A2 | 5/1995 |
|---|---|---|
| JP | 4-218384 | 8/1992 |
| JP | 6-141876 | 5/1994 |
| JP | 654534 A2 | 5/1995 |
| JP | 8-89261 | 4/1996 |
| JP | 8-89261 A | 4/1996 |
| JP | 10-150997 | 6/1998 |
| JP | 11-215995 | 8/1999 |
| JP | 03-31636 A1 | 4/2003 |
| WO | WO 03/031636 A1 | 4/2003 |

OTHER PUBLICATIONS

Inference of protein function from protein structure, Pal et al. Structure, 2005, 13, pp. 121-130.*

Li, Zhi, et al., "Preparation of optically active N-benzyl-3-hydroxypyrrolidine by enzymatic hydroxylation," Tetrahedron: Asymmetry, 10 (1999) 1323-1333.

* cited by examiner

Primary Examiner—Nashaat T Nashed
Assistant Examiner—Younus Meah
(74) Attorney, Agent, or Firm—Sughrue Mion, PLLC

(57) ABSTRACT

The present invention provides a novel polypeptide efficiently forming (R)-N-benzyl-3-pyrrolidinol, a polynucleotide coding for said polypeptide, and use of the same. The present invention relates to a polypeptide having the physical and chemical properties (1) to (4): (1) activity acting on N-benzyl-3-pyrrolidinone with NADH or NADPH as a coenzyme, to form (R)-N-benzyl-3-pyrrolidinol; (2) optimum pH of 5.5 to 6.0 for activity ; (3) optimum temperature of 50° C. to 55° C. for activity ; (4) molecular weight of about 55,000 as determined by gel filtration analysis, and about 28,000 as determined by SDS polyacrylamide gel electrophoresis analysis. The present invention also relates to a polypeptide comprising the amino acid sequence of SEQ ID NO:1, a polynucleotide coding for said polypeptide, and a transformant producing said polypeptide at high levels.

17 Claims, 2 Drawing Sheets

Fig. 1

```
  1 ATGTCCCAGGATTTTTCAGGCAAGGTCGCATTCGTAACGGGTGGTGCCTCGGGCATCGGT   60
    M  S  Q  D  F  S  G  K  V  A  F  V  T  G  G  A  S  G  I  G

61 GAGGCGGTCGTCAAGCAGCTTGCCGCGCGCGGCGCCAAGGTTGTGGTTGCCGATCTCAAG  120
    E  A  V  V  K  Q  L  A  A  R  G  A  K  V  V  V  A  D  L  K

121 CTCGAAGGCGCGCAGGCGGTTGCCGATGCGGTCAAGGCCGCCGGCGGCGAAGCGGCCGCG  180
    L  E  G  A  Q  A  V  A  D  A  V  K  A  A  G  G  E  A  A  A

181 GTAGCTGTCGATGTCGCCAAGGCCGATCAGGTGGAGAAGGCTGTCCAGTTCGCCGTCGAC  240
    V  A  V  D  V  A  K  A  D  Q  V  E  K  A  V  Q  F  A  V  D

241 ACCTTTGGCGCCCTGCATCTGGCGGTCAATAATGCCGGCATTGGCGGCGCTTCCGCTCCC  300
    T  F  G  A  L  H  L  A  V  N  N  A  G  I  G  G  A  S  A  P

301 CTCGGCGATTATTCCTTCGACGACTGGCATAGGGTTATCGACGTCAATCTCAATTCCGTC  360
    L  G  D  Y  S  F  D  D  W  H  R  V  I  D  V  N  L  N  S  V

361 TTCTATTCGATGAAGTACGAGATCGTCGCCATGCTCAGGGCAGGCGGTGGCGCCATCGTC  420
    F  Y  S  M  K  Y  E  I  V  A  M  L  R  A  G  G  A  I  V

421 AACATGGCCTCCATCCTCGGCTCGGTGACCTTTCCCAATGCACCGGCCTATGTCACCGCC  480
    N  M  A  S  I  L  G  S  V  T  F  P  N  A  P  A  Y  V  T  A

481 AAGCACGGCGTGGTCGGCATGACCAAGTCGGCCGCGGTGGACTATGCCAAAAAGGGCATT  540
    K  H  G  V  V  G  M  T  K  S  A  A  V  D  Y  A  K  K  G  I

541 CGCGTCACGGCCGTCGGGCCCGGTTTCATCGACACGCCGCTCCTATCCGCCTTGCCCAAG  600
    R  V  T  A  V  G  P  G  F  I  D  T  P  L  L  S  A  L  P  K

601 GAAACCCTGGACTACCTCAAATCCGTCCATCCGATCGGACGGCTGGGTACCTCGGATGAA  660
    E  T  L  D  Y  L  K  S  V  H  P  I  G  R  L  G  T  S  D  E

661 GTCGCAGCGCTGACCGCGTTCCTGCTCTCCGATGCAGCGTCGAACATCACCGGCTCCTAT  720
    V  A  A  L  T  A  F  L  L  S  D  A  A  S  N  I  T  G  S  Y

721 CACCTGGTCGATGGCGGCTACGTCGCCCAATAG   753
    H  L  V  D  G  G  Y  V  A  Q  *
```

CARBONYL REDUCTASE, GENE THEREOF AND METHOD OF USING THE SAME

CROSS-REFERENCE TO RELATED APPLICATIONS

This application is a divisional of U.S. application Ser. No. 10/528,000, filed Mar. 21, 2005 (issued May 22, 2007 as U.S. Pat. No 7,220,564), which is a National Stage of PCT/JP2003/11957, filed Sep. 19, 2003 claiming benefit under 35 U.S.C. § 119 from Japanese Patent Application No. 2002-0272976, filed on Sep. 19, 2002, the entire contents of which are incorporated herein by reference.

The present invention relates to a polypeptide having activity in stereoselectively reducing N-benzyl-3-pyrrolidinone represented by the formula (1):

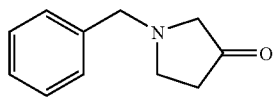

(1)

to form (R)-N-benzyl-3-pyrrolidinol represented by the formula (2):

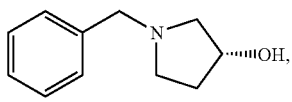

(2)

a polynucleotide coding for said polypeptide, an expression vector containing said polynucleotide, and a transformant transformed with said expression vector.

The present invention also relates to a method for producing optically active alcohols, in particular optically active N-benzyl-3-pyrrolidinol, optically active 2-tetralol derivatives and optically active 1-phenylethanol derivatives using the above transformant. Such optically active N-benzyl-3-pyrrolidinol, optically active 2-tetralol derivatives, and optically active 1-phenylethanol derivatives are compounds useful as synthetic materials for such as medicines and pesticides.

BACKGROUND ART

As for the methods for producing optically active N-benzyl-3-pyrrolidinol, there have been known the method of producing optically active N-benzyl-3-pyrrolidinol which comprises stereoselectively reducing N-benzyl-3-pyrrolidinone in the presence of an enzyme having activity in stereoselectively reducing N-benzyl-3-pyrrolidinone (Japanese Kokai Publication Hei-06-141876), and the method for producing optically active N-benzyl-3-pyrrolidinol which comprises allowing cells of microorganisms such as the genus *Depodascus*, cultured products, or processed products thereof to act on N-benzyl-3-pyrrolidinone (Japanese Kokai Publication Hei-10-150997).

Moreover, as the methods for producing optically active 2-tetralol derivatives, there has been known the method comprising allowing baker's yeast to act on 2-tetralone derivatives having a substituent on a benzene ring to produce the corresponding optically active 2-tetralol derivatives (Tetrahedron 51, 11531, (1995)).

Moreover, as for the methods for producing optically active 1-phenylethanol derivatives, there have been known the method comprising allowing a microorganism belonging to the genus *Ashbya* or *Ogataea*, for instance, or processed products thereof to act on a 2-halo-1-(substituted phenyl) ethanone to form an optically active 2-halo-1-(substituted phenyl)ethanol (Japanese Kokai Publication Hei-04-218384 and Japanese Kokai Publication Hei-11-215995), and the method comprising allowing dry cells of *Geotrichum candidum* to act on a 1-(substituted phenyl)ethanone to form an optically active 1-(substituted phenyl)ethanol (J. Org. Chem., 63, 8957 (1998)).

However, all of these methods allow only a low substrate concentration or give a low rate of conversion from substrate to product. Thus, more efficient production method has been desired.

SUMMARY OF THE INVENITON

In view of the above-mentioned state of the art, the present invention has for its object to provide a polypeptide useful in the production of various optically active alcohols including optically active N-benzyl-3-pyrrolidinol, optically active 2-tetralol derivatives and optically active 1-phenylethanol derivatives, a polynucleotide coding for the above polypeptide, an expression vector containing the above polynucleotide, and a transformant transformed with the above expression vector.

The present invention also has for its object to provide a method for efficiently producing various optically active alcohols including optically active N-benzyl-3-pyrrolidinol, optically active 2-tetralol derivatives and optically active 1-phenylethanol derivatives by using the above-mentioned transformant.

The present inventors isolated a polypeptide having activity in stereoselectively reducing N-benzyl-3-pyrrolidinone to form (R)-N-benzyl-3-pyrrolidinol, from a microorganism having such activity. And they found that use of said polypeptide make it possible to efficiently produce not only optically active N-benzyl-3-pyrrolidinol but also useful optically active alcohol, such as optically active 2-tetralol derivatives and optically active 1-phenylethanol derivatives. They also succeeded in isolating a polynucleotide coding for said polypeptide and further in creating an expression vector and a transformant. Thus, the present invention has been completed.

That is, the invention provides a polypeptide capable of stereoselectively reducing N-benzyl-3-pyrrolidinone to form (R)-N-benzyl-3-pyrrolidinol.

The invention also provides a polynucleotide coding for the above polypeptide.

The invention further provides an expression vector containing the above polynucleotide.

The invention further provides a transformant capable of producing the above polypeptide at high levels.

The invention still further provides a practical method for producing useful optically active alcohols including optically active N-benzyl-3-pyrrolidinol, optically active 2-tetralol derivatives and optically active 1-phenylethanol derivatives using said transformant.

DETAILED DESCRIPTION OF THE INVENTION

In the following, the invention is described in detail.

Usable as the polypeptide of the invention is a polypeptide having the following physical and chemical properties (1) to (4):

(1) stereoselectively reducing N-benzyl-3-pyrrolidinone represented by the following formula (1):

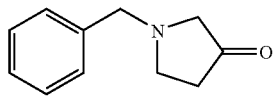

with NADH or NADPH as a coenzyme, to form (R)-N-benzyl-3-pyrrolidinol represented by the following formula (2):

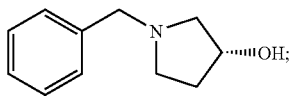

(2) optimum pH for activity of 5.5 to 6.0;
(3) optimum temperature for activity of 50° C. to 55° C.;
(4) molecular weight of about 55,000 as determined by gel filtration analysis, about 28,000 as determined by SDS polyacrylamide gel electrophoresis analysis.

As the polypeptide of the invention, there may further be mentioned, for example, (a) a polypeptide comprising the amino acid sequence shown under SEQ ID NO:1 in the sequence listing or (b) a polypeptide comprising the amino acid sequence shown under SEQ ID NO:1 in the sequence listing or an amino acid sequence resulting from substitution, insertion, deletion or addition of one or several amino acid residues in the amino acid sequence shown under SEQ ID NO:1 in the sequence listing and having activity in stereoselectively reducing N-benzyl-3-pyrrolidinone to form (R)-N-benzyl-3-pyrrolidinol.

Polypeptides comprising an amino acid sequence derived from the amino acid sequence shown under SEQ ID NO:1 in the sequence listing having substitution, insertion, deletion or addition of one or several amino acids can be prepared by the conventional method described in Current Protocols in Molecular Biology (John Wiley and Sons, Inc., 1989), and the like. So long as they have activity in stereoselectively reducing N-benzyl-3-pyrrolidinone to form (R)-N-benzyl-3-pyrrolidinol, such polypeptides are included within the definition of the polypeptide of the invention.

Such a polypeptide can be isolated from a microorganism having the activity mentioned above. The microorganism to be used as the source of the polypeptide of the invention is not particularly restricted but there may be mentioned, for example, microorganisms of the genus *Devosia*, and *Devosia riboflavina* IFO 13584 is particularly preferred.

The microorganism producing the polypeptide of the invention may be a wild strain or variant. A microorganism derived by a genetic engineering technique, such as cell fusion or gene manipulation can be used as well.

A genetically engineered microorganism producing the polypeptide of the invention can be obtained, for example, by a method comprising the step of isolating and/or purifying such polypeptide and determining a part or the whole of the amino acid sequence thereof, the step of determining the polynucleotide base sequence coding for the polypeptide based on that amino acid sequence, and the step of obtaining a recombinant microorganism by introducing that polynucleotide into another microorganism.

The polypeptide of the invention can be purified from the microorganism containing that polypeptide in the conventional manner. For example, cells of the microorganism are cultivated in an appropriate medium, and cells are then collected from the culture by centrifugation. The cells obtained are disrupted using a sonicator, for instance, and the cell residue is removed by centrifugation, whereby a cell-free extract is obtained. The polypeptide can be purified from this cell-free extract by using such techniques, either singly or in combination, as salting out (e.g. by ammonium sulfate precipitation, sodium phosphate precipitation, etc.), precipitation using a solvent (protein fractionation precipitation with acetone, ethanol, etc.), dialysis, gel filtration, ion exchange, reversed phase or like column chromatography, and ultrafiltration.

The enzyme activity can be determined and calculated by adding the substrate N-benzyl-3-pyrrolidinone (5 mM), the coenzyme NADPH (0.25 mM) and the enzyme to 100 mM phosphate buffer (pH 6.5) and measuring the decrease in absorbance at a wavelength of 340 nm at 30° C.

While any polynucleotide coding for the above polypeptide can be used as the polynucleotide of the invention, there may be mentioned, for example, (c) the polynucleotide comprising the base sequence shown under SEQ ID NO:2 in the sequence listing or (d) a polynucleotide capable of hybridizing with a polynucleotide comprising the base sequence complementary to the base sequence shown under SEQ ID NO:2 in the sequence listing under stringent conditions and coding for a polypeptide having activity in stereoselectively reducing N-benzyl-3-pyrrolidinone represented by the above formula (1) to form (R)-N-benzyl-3-pyrrolidinol represented by the above formula (2).

The polynucleotide capable of hybridizing with a polynucleotide comprising the base sequence complementary to the base sequence shown under SEQ ID NO:2 in the sequence listing under stringent conditions means a polynucleotide obtained by colony hybridization, plaque hybridization, or southern hybridization, for instance, using a polynucleotide comprising the base sequence complementary to the base sequence shown under SEQ ID NO:2 in the sequence listing as a probe. More specifically, there may be mentioned a polynucleotide that can be identified after carrying out hybridization using a filter with colony- or plaque-derived polynucleotides immobilized thereon, in the presence of 0.7 to 1.0 M NaCl at 65° C., and washing the filter with 0.1 to 2×SSC solution (the composition of 1×SSC solution comprising 150 mM sodium chloride and 15 mM sodium citrate) at 65° C.

The hybridization can be carried out as described in Molecular Cloning, A laboratory manual, second edition (Cold Spring Harbor Laboratory Press, 1989), and the like.

As the polynucleotide capable of hybridizing, there may be mentioned, specifically, polynucleotides having at least 60%, preferably at least 80%, more preferably at least 90%, still more preferably at least 95%, most preferably at least 99%, homology in sequence to the polynucleotide shown under SEQ ID NO:2 in the sequence listing and, so long as the polypeptides encoded have activity in stereoselectively reducing N-benzyl-3-pyrrolidinone to form (R)-N-benzyl-3-pyrrolidinol, they are included within the definition of the polynucleotide of the invention.

The "homology (%) in sequence" so referred to herein is expressed in terms of the value determined by aligning, in an optimum manner, the two polynucleotides to be compared, determining the number of those sites of coincidence in nucleic acid base (e.g. A, T, C, G, U or I) between the both, dividing the number by the total number of the bases compared, and multiplying the result by 100.

The sequence homology can be calculated, for example, by using the following tools for sequence analysis: GCG Wisconsin Package (Program Manual for the Wisconsin Package, Version 8, September, 1994, Genetics Computer Group, 575 Science Drive Madison, Wis., USA 53711; Rice, P. (1996), Program Manual for EGCG Package, Peter Rice, The Sanger Centre, Hinxton Hall, Cambridge, CB10 1RQ, England) and the ExPASy World Wide Web Server for Molecular Biology (Geneva University Hospital and University of Geneva, Geneva, Switzerland).

The polynucleotide of the invention can be obtained from a microorganism having activity in stereoselectively reducing N-benzyl-3-pyrrolidinone to form (R)-N-benzyl-3-pyrrolidinol. As such microorganism, there may be mentioned, for example, microorganisms of the genus *Devosia*, and *Devosia riboflavina* IFO 13584 may be mentioned as a particularly preferred one.

In the following, an example is described of the method for obtaining the polynucleotide of the invention from a microorganism having activity in stereoselectively reducing N-benzyl-3-pyrrolidinone to form (R)-N-benzyl-3-pyrrolidinol. This example is not restrictive of the scope of the invention, however.

First, partial amino acid sequences of the above-mentioned polypeptide after purification and peptide fragments obtained by digestion of said polypeptide with appropriate endopeptidases are determined by the Edman method. Based on this amino acid sequence information, nucleotide primers are synthesized. Then, the chromosomal DNA of the microorganism to serve as the source of the polynucleotide of the invention is prepared from that microorganism by the conventional method of DNA isolation such as the method described in Current Protocols in Molecular Biology (John Wiley and Sons, Inc., 1989).

Using this chromosomal DNA as a template, PCR (polymerase chain reaction) is carried out using the nucleotide primers mentioned above to thereby amplify part of the polynucleotide coding for the polypeptide. The base sequence of the thus-amplified polynucleotide can be determined by the dideoxy sequencing method, dideoxy chain termination method, or the like. For example, this can be carried out using ABI PRISM Dye Terminator Cycle Sequencing Ready Reaction Kit (product of PerkinElmer) and ABI 373A DNA Sequencer (product of PerkinElmer).

Once part of the base sequence of the polynucleotide coding for said polypeptide has become clear, the base sequence of the whole can be determined, for example, by the i-PCR method (Nucl. Acids Res., 16, 8186 (1988)). When the polynucleotide on the chromosomal DNA contains an intron or introns, the base sequence of the intron-free mature polynucleotide can be determined, for example, by the following method.

Thus, first, from a microorganism to serve as the origin of the polynucleotide, mRNA of the microorganism is prepared by the conventional method of nucleotide isolation such as the method described in Current Protocols in Molecular Biology (John Wiley and Sons, Inc., 1989). Then, using this mRNA as a template, a mature polynucleotide is amplified by the RT-PCR method (Proc. Natl. Acad. Sci. USA, 85, 8998 (1988)) using nucleotide primers respectively having the sequences around the 5' and 3' ends of said polynucleotide that have been made clear in advance, and the base sequence of the mature polypeptide is determined in the same manner as described above.

As the vector used for introducing the nucleotide of the invention into a host microorganism and expressing the same in the host microorganism, any of vectors capable of expressing the gene in said polynucleotide in an appropriate host microorganism may be used. As such vectors, there may be mentioned, for example, ones selected from among plasmid vectors, phage vectors and cosmid vectors. Further, shuttle vectors capable of gene exchange with another host strain may also be used.

Such vectors generally contain such regulatory factors as the lacUV5 promoter, trp promoter, trc promoter, tac promoter, lpp promoter, tufB promoter, recA promoter and pL promoter and can be suitably used as expression vectors containing an expression unit operatively connected with the polynucleotide of the invention.

The term "regulatory factors" as used herein means a base sequence comprising a functional promoter and arbitrary related transcription elements (e.g. enhancer, CCAAT box, TATA box, SPI locus).

The phrase "operatively connected" as used herein means that the polynucleotide is connected with various regulatory elements controlling the expression thereof, inclusive of a promoter, an enhancer and so forth, so that the whole can operate in host cells and the gene in said polynucleotide can be expressed. It is well known to those skilled in the art that the types and species of the regulatory factors may vary according to the host cells.

As the host cells into which the expression vector containing the polynucleotide of the invention is to be introduced, there may be mentioned bacteria, yeasts, fungi, plant cells and animal cells, and the like. *Escherichia coli* cells are particularly preferred, however.

The expression vector containing the polynucleotide of the invention can be introduced into host cells in the conventional manner. When *Escherichia coli* cells are used as the host cells, the expression vector containing the polynucleotide of the invention can be introduced thereinto by the calcium chloride method, for instance.

When (R)-N-benzyl-3-pyrrolidinol is to be produced by stereoselectively reducing N-benzyl-3-pyrrolidinone using the polypeptide of the invention, a coenzyme such as NADH or NADPH is required. Coenzymes generally require equivalent moles to the substrate, however, when an enzyme capable of converting the oxidized coenzyme to the reduced form (such ability hereinafter referred to as "coenzyme regenerating ability") is added to the reaction system together with the substrate thereof, namely when the reaction is carried out using the coenzyme regenerating system in combination with the polypeptide of the invention, the usage of the expensive coenzyme can be markedly reduced.

Usable as the enzyme having coenzyme regenerating ability are, for example, hydrogenase, formate dehydrogenase, alcohol dehydrogenase, aldehyde dehydrogenase, glucose-6-phosphate dehydrogenase and glucose dehydrogenase. Glucose dehydrogenase is preferably used.

The asymmetric reduction reaction can be carried out by separately adding the above-mentioned enzyme having coenzyme regenerating ability to the reaction system. It is possible to carry out the reaction efficiently by using, as a catalyst, a transformant as transformed with both the polynucleotide of the invention and a polynucleotide coding for a polypeptide having coenzyme regenerating ability, without separately preparing an enzyme having coenzyme regenerating ability and adding the same to the reaction system.

Such a transformant can be obtained by inserting the polynucleotide of the invention and a polynucleotide coding for a polypeptide having coenzyme regenerating ability (e.g. glucose dehydrogenase) into one and the same vector and introducing the resulting recombinant vector into host cells or, further, by inserting these two polynucleotides respectively into two vectors belonging to different incompatible groups and introducing the resulting two vectors into the same host cells.

The expression vector of the invention contains the above-mentioned polynucleotide, as described above. As a preferred example of the expression vector, there may be mentioned a plasmid pNTDR.

As the expression vector of the invention, there may also be mentioned one further containing a polynucleotide coding for the above-mentioned polypeptide having glucose dehydrogenase activity. The glucose dehydrogenase derived from *Bacillus megaterium* is preferred as the polypeptide having glucose dehydrogenase activity. More preferred is an expression vector which is a plasmid pNTDRG1.

The transformant of the invention is obtained by transforming host cells using the above expression vector. *Escherichia coli* cells are preferred as the above host cells.

*E. coli* HB101(pNTDR) and *E. coli* HB101(pNTDRG1), which are typical transformants of the invention, have been internationally deposited, as of Aug. 25, 2003, with the National Institute of Advanced Industrial Science and Technology International Patent Organism Depositary, Central 6, 1-1-1 Higashi, Tsukuba, Ibaraki, Japan, under the accession numbers FERM BP-08457 and FERM BP-08458, respectively, under the Budapest Treaty.

The activity of the enzyme having coenzyme regenerating ability in the transformant can be measured in the conventional manner. For example, the glucose dehydrogenase activity can be determined by adding 0.1 M of the substrate glucose, 2 mM of the coenzyme NADP and the enzyme to 1 M Tris hydrochloride buffer (pH 8.0) and measuring the increase in absorbance at a wavelength 340 nm at 25° C.

The production of an optically active alcohol, such as an optically active N-benzyl-3-pyrrolidinol, optically active 2-tetralol derivatives or optically active 1-phenylethanol derivatives, using the transformant of the invention can be carried out as follows. That is, the culture of the above transformant or a processed product thereof is reacted with a carbonyl group-containing compound to obtain an optically active alcohol.

The carbonyl group-containing compound to serve as the substrate, such a coenzyme as NADH and the culture of the transformant or a processed product thereof, and the like are first added to an appropriate solvent, and the reaction is allowed to proceed with stirring under pH adjustment.

The transformant can be cultivated using liquid nutrient media containing ordinary carbon sources, nitrogen sources, inorganic salts, organic nutrients and so forth so long as the microorganism can grow thereon. The cultivation temperature is preferably 4 to 50° C.

As the processed product of the transformant and the like there may be mentioned, for example, crude extracts, cultured cells, lyophilized cells, acetone-dried cells, and products derived therefrom by grinding. It is also possible to use the polypeptide itself or cells as such in a form immobilized by a method known in the art.

When a transformant producing both the polypeptide of the invention and an enzyme having coenzyme regenerating ability (e.g. glucose dehydrogenase) is used in carrying out the reaction, it is possible to markedly reduce the amount of use of the coenzyme by adding, to the reaction system, a substrate (e.g. glucose) for coenzyme regeneration.

As the carbonyl group-containing compound, which is the substrate, there may be mentioned, for example, N-benzyl-3-pyrrolidinone represented by the formula (1):

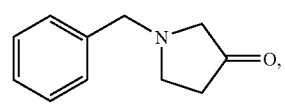

2-tetralone derivatives represented by the general formula (3):

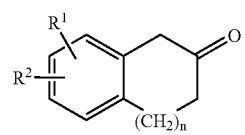

in the formula, $R^1$ and $R^2$ may be the same or different and each represents a hydrogen atom or an alkoxy group, and n represents 1 or 2, or 1-phenyl ethanone derivatives represented by the general formula (5):

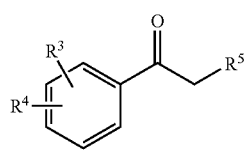

in the formula, $R^3$ and $R^4$ may be the same or different and each represents a hydrogen or halogen atom or an alkoxy or nitro group, $R^5$ represents a hydrogen or halogen atom, a hydroxyl group or an alkyl group, which may optionally be substituted. As the compounds represented by the formulae (3) and (5), for more detail, there may be mentioned 7-methoxy-2-tetralone, 3-methoxy-6,7,8,9-tetrahydro-5H-benzocycloheptene-6-one, 2-chloro-1-(4'-fluorophenyl) ethanone, and 2-chloro-1-(3'-chlorophenyl)ethanone, for example.

As the optically active alcohol obtainable by the method mentioned above, there may be mentioned, for example, (R)-N-benzyl-3-pyrrolidinol represented by the formula (2):

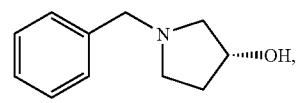

2-tetralol derivatives represented by the general formula (4):

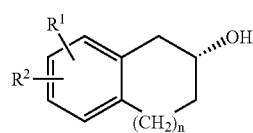

in the formula, $R^1$, $R^2$ and n are as defined above, or 1-phenylethanol derivatives represented by the general formula (6):

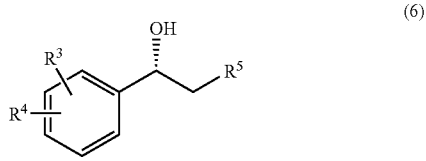

(6)

in the formula, $R^3$, $R^4$ and $R^5$ are as defined above. As the compounds represented by the formulae (4) and (6), for more detail, there may be mentioned 7-methoxy-2-tetralol, 3-methoxy-6,7,8,9-tetrahydro-5H-benzocycloheptene-6-ol, 2-chloro-1-(4'-fluorophenyl)ethanol, or 2-chloro-1-(3'-chlorophenyl)ethanol, for example.

As the alkoxy group represented by $R^1$, $R^2$, $R^3$ and/or $R^4$, there may be mentioned alkoxy groups containing 1 to 3 carbon atoms, for example, methoxy, ethoxy, propoxy group, etc., with methoxy group being preferred.

As the halogen atom represented by $R^3$, $R^4$ and/or $R^5$, there may be mentioned, for example, a fluorine, chlorine, bromine or iodine atom.

As the alkyl group which may optionally be substituted represented by $R^5$, there may be mentioned alkyl groups containing 1 to 8 carbon atoms, for example methyl, ethyl, propyl, hexyl, octyl group, etc. Preferred is an alkyl group containing 1 or 2 carbon atoms. As the substituent(s) of the alkyl group which may optionally be substituted represented by $R^5$, there may be mentioned fluorine, chlorine and bromine atoms, hydroxyl and amino groups, and the like.

In carrying out the reaction, aqueous solvent or a mixture of an aqueous solvent and an organic solvent may be used. As the organic solvent, there may be mentioned, for example, toluene, hexane, diisopropyl ether, n-butyl acetate, ethyl acetate, and the like.

The reaction temperature is 10° C. to 70° C., preferably 20 to 40° C., and the reaction time is 1 to 100 hours, preferably 10 to 50 hours. During the reaction, the pH of the reaction mixture is maintained at 4 to 10, preferably 5 to 8, using hydrochloride acid, an aqueous solution of sodium hydroxide, an aqueous solution of sodium carbonate, for instance.

The reaction can be carried out either batchwise or continuously. In the batchwise case, the reaction substrate is added to a charge concentration of 0.1% to 70% (w/v).

The optically active alcohol formed by the reaction can be purified in the conventional manner. When the optically active alcohol formed by the reaction is N-benzyl-3-pyrrolidinol, 7-methoxy-2-tetralol, 3-methoxy-6,7, 8,9-tetrahydro-5H-benzocycloheptene-6-ol, 2-chloro-1-(4'-fluorophenyl) ethanol, or 2-chloro-1-(3'-chlorophenyl)ethanol, for instance, the suspended matter including microbial cells and the like is removed from the reaction mixture by centrifugation, filtration or like treatment according to need, the pH is adjusted to 3 to 11 suited for extraction using a sodium hydroxide solution, sodium carbonate solution, hydrochloric acid, and the like, the product is then extracted with such an organic solvent as ethyl acetate or toluene, and the organic solvent is then removed under reduced pressure. The product can be further purified by subjecting to such a treatment as distillation, crystallization and/or chromatography.

The quantitation of N-benzyl-3-pyrrolidinone and N-benzyl-3-pyrrolidinol can be carried out by gas chromatography (column: GL Sciences Inc.'s UniportB 10% PEG-20M (ID 3.0 mm×1.0 m), column temperature: 200° C., career gas: nitrogen, detection: FID)).

The determination of the optical purity of N-benzyl-3-pyrrolidinol can be carried out by high-performance liquid column chromatography (column: Daicel Chemical Industries' Chiralcel OB (ID 4.6 mm×250 mm), eluent: n-hexane/isopropanol/diethyl amine=99/1/0.1, flow rate: 1 ml/min, detection: 254 nm, column temperature: room temperature).

The quantitation of 7-methoxy-2-tetralone, 3-methoxy-6,7,8,9-tetrahydro-5H-benzocycloheptene-6-one, 7-methoxy-2-tetralol and 3-methoxy-6,7,8,9-tetrahydro-5H-benzocycloheptene-6-ol was carried out by high-performance liquid column chromatography (column: Nacalai Tesque's COSMOSIL 5C8-MS (ID 4.6 mm×250 mm), eluent: water/acetonitrile=1/1, flow rate: 1 ml/min, detection; 210 nm, column temperature: room temperature).

The optical purity of 7-methoxy-2-tetralol and 3-methoxy-6,7,8,9-tetrahydro-5H-benzocycloheptene-6-ol was determined by high-performance liquid column chromatography (column: Daicel Chemical Industries' Chiralcel OJ (ID 4.6 mm×250 mm), eluent: n-hexane/isopropanol=9/1, flow rate: 1 ml/min, detection: 254 nm, column temperature: room temperature).

The quantitation of 2-chloro-1-(4'-fluorophenyl)ethanone, 2-chloro-1-(3'-chlorophenyl)ethanone, 2-chloro-1-(4'-fluorophenyl)ethanol and 2-chloro-1-(3'-chlorophenyl)ethanol was carried out by high-performance liquid column chromatography (column: YMC Co., Ltd.'s YMC-Pack ODS A-303 (ID 4.6 mm×250 mm), eluent: water/acetonitrile=1/1, flow rate: 1 ml/min, detection; 210 nm, column temperature: room temperature).

The optical purity of 2-chloro-1-(4'-fluorophenyl)ethanol and 2-chloro-1-(3'-chlorophenyl)ethanol was determined by high-performance liquid column chromatography (column: Daicel Chemical Industries' Chiralcel OJ (ID 4.6 mm×250 mm), eluent: n-hexane/isopropanol=39/1, flow rate: 1 ml/min, detection: 254 nm, column temperature: room temperature).

In accordance with the present invention, the polypeptide of the invention can be produced in an efficient manner and a method for producing various useful optically active alcohols is provided, as described above.

BRIEF DESCRIPTION OF THE DRAWINGS

FIG. 1 shows the polynucleotide sequence of the invention and the amino acid sequence deduced therefrom.

BEST MODE FOR CARRYING OUT THE INVENTION

Figure 2:
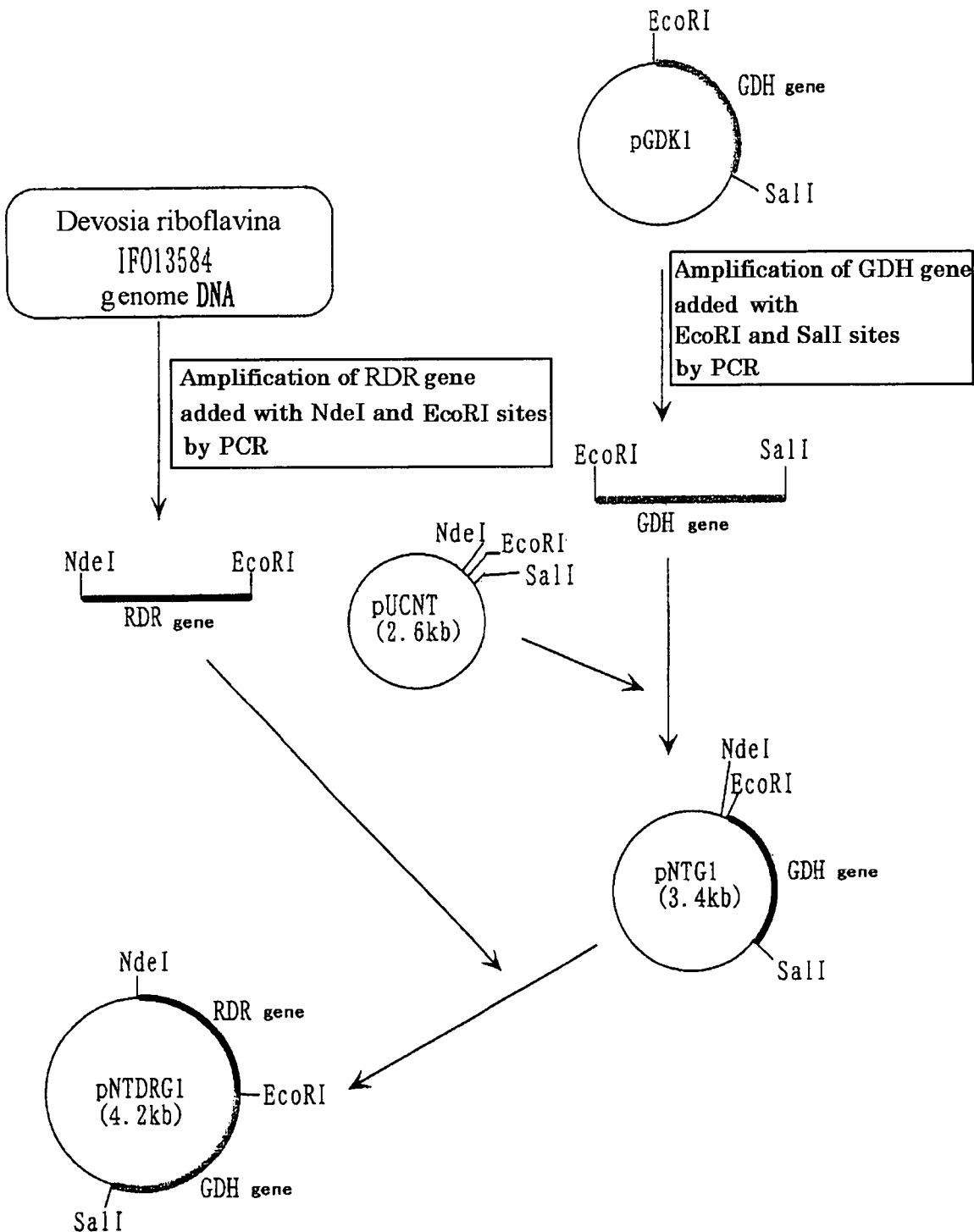
FIG. 2 shows a method for constructing a recombinant plasmid pNTDRG1 and the structure thereof.

The following examples illustrate the present invention in detail. They are, however, by no means limitative of the scope of the invention. The details of the procedures in the recombinant DNA technology as used in the following examples are described in the following monographs:

Molecular Cloning, 2nd Edition (Cold Spring Harbor Laboratory Press, 1989); Current Protocols in Molecular Biology (Greene Publishing Associates and Wiley-Interscience).

EXAMPLE 1

Enzyme Purification

An enzyme having activity in stereoselectively reducing N-benzyl-3-pyrrolidinone to form (R)-N-benzyl-3-pyrrolidinol was singly purified from *Devosia riboflavina* IFO 13584 according to the method described below. Unless otherwise specified, the purification procedure was carried out at 4° C.

(Cultivation of *Devosia riboflavina* IFO 13584)

400 ml of a liquid medium having the composition specified below was dispensed to 72 of 2 L Sakaguchi flasks and subjected to steam sterilization at 120° C. for 20 minutes.

Medium Composition (% being indicated as (w/v)):

| Polypeptone | 1.0% |
| Yeast extract | 0.3% |
| Meat extract | 0.3% |
| Malt extract | 1.0% |
| NaCl | 0.3% |
| Adekanol LG-109 (product of NOF Corp.) | 0.003% |
| Tap water | pH 7.0 |

This medium was inoculated with a culture containing *Devosia riboflavina* IFO 13584 by 5 ml which has been precultured in advance in the same medium, and shaking cultivation was carried out at 30° C. for 48 hours.

(Preparation of a Cell-free Extract)

Cells were collected from a 28,000 ml portion of the above culture by centrifugation and washed with saline to obtain 363 g of wet cells of the strain mentioned above. The wet cells were suspended in 500 ml of 100 mM phosphate buffer (pH 7.0) and subjected to ultrasonic cell disruption using an ultrasonic disruption machine SONIFIRE 250 (product of BRANSON). Cell residue was removed from the disruption product by centrifugation to obtain 840 ml of cell-free extract.

(Heat Treatment and Acid Treatment of Cell-free Extract)

A beaker containing the above cell-free extract was immersed in a thermostat bath at 60° C., stirred for 25 minutes, and then cooled to 4° C. in an ice bath. After removing the resulting precipitate by centrifugation, the pH of the centrifugation supernatant was adjusted to 5.0 using phosphoric acid, and stirred for 3 hours in an ice bath. The resulting precipitate was again removed by centrifugation to obtain 830 ml of a crude enzyme solution.

(Ammonium Sulfate Fractionation)

The pH of the crude enzyme solution obtained as above was adjusted to 7.0 using aqueous ammonia, and ammonium sulfate was added to and dissolved therein to attain 35% saturation, and the resulting precipitate was removed by centrifugation (on that occasion, the pH of the crude enzyme solution was maintained at 7.0 with aqueous ammonia). While maintaining the pH at 7.0 in the same manner as in the above step, ammonium sulfate was further added to and dissolved in the supernatant resulting from centrifugation to attain 55% saturation, and the resulting precipitate was collected by centrifugation. This precipitate was dissolved in 50 ml of 10 mM phosphate buffer (pH 7.0), the solution was dialyzed overnight with the same buffer to obtain 83 ml of a crude enzyme solution.

(DEAE-TOYOPEARL Column Chromatography)

The pH of the crude enzyme solution obtained by the above ammonium sulfate fractionation was adjusted to 8.0 using aqueous ammonia. This was applied to a DEAE-TOYOPEARL 650M (product of Tosoh Corporation) column (250 ml) equilibrated in advance with 10 mM phosphate buffer (pH 8.0) to elute an active fraction with the same buffer. The active fraction was collected and added with phosphoric acid to adjust the pH to 7.0.

(Phenyl-TOYOPEARL Column Chromatography)

Ammonium sulfate was dissolved in the crude enzyme solution obtained in the above DEAE-TOYOPEARL column chromatography to a final concentration of 1 M (while maintaining the pH of the crude enzyme solution at 7.0 with adding aqueous ammonia), and the solution was applied, for active fraction adsorption, to a Phenyl-TOYOPEARL 650M (product of Tosoh Corporation) column (100 ml) equilibrated in advance with 10 mM phosphate buffer (pH 7.0) containing 1 M ammonium sulfate. After washing the column with the same buffer, the active fraction was eluted at a linear gradient of ammonium sulfate (from 1 M to 0 M). The active fraction was collected and dialyzed overnight with 10 mM phosphate buffer (pH 7.0) to obtain a purified enzyme preparation showing a single spot in electrophoresis. Hereinafter, this enzyme is referred to as RDR.

EXAMPLE 2

Determination of Enzyme Properties

RDR obtained in Example 1 was investigated as to its enzymatic properties. Fundamentally, the enzyme activity was measured by adding the substrate N-benzyl-3-pyrrolidinone (5 mM), the coenzyme NADPH (0.25 mM) and the enzyme to 100 mM phosphate buffer (pH 6.5), allowing the reaction to proceed at 30° C. for 1 minute, and then measuring the decrease in absorbance at a wavelength of 340 nm.

(1) Activity:

In the presence of NADH as a coenzyme, the enzyme acted on N-benzyl-3-pyrrolidinone to form (R)-N-benzyl-3-pyrrolidinol with an optical purity of 99.9% ee or more. The enzyme activity measured with NADPH as a coenzyme by the above method was about 0.6% of the activity obtained by using NADH as a coenzyme.

(2) Optimum pH for Activity:

Enzyme activity measurements were carried out by the same enzyme activity measurement method as mentioned above except that the pH was varied in the range of 4.0 to 8.0 using, as the buffer, 100 mM phosphate buffer and 100 mM acetate buffer. As a result, the optimum pH for the action on N-benzyl-3-pyrrolidinone was found to be 5.5 to 6.0.

(3) Optimum Temperature for Activity:

Enzyme activity measurements were carried out by the same enzyme activity measurement method as mentioned above except that the temperature was varied from 20° C. to 60° C. As a result, the optimum temperature for the action on N-benzyl-3-pyrrolidinone was found to be 50° C. to 55° C.

(4) Molecular Weight:

The purified enzyme RDR was subjected to gel filtration chromatography analysis on TSK-GEL G3000 SWXL column (product of Tosoh Corporation) using 50 mM phosphate buffer (pH 7.0) containing 150 mM sodium chloride as an eluent. As a result, this enzyme was found to have a molecular weight of about 55,000 as calculated from its relative retention time as compared with standard proteins. The subunit molecular weight of the enzyme was calculated from the mobility values relative to standard proteins as obtained by SDS-polyacrylamide gel electrophoresis. The subunit molecular weight of the enzyme was about 28,000.

EXAMPLE 3

RDR Gene Cloning (PCR Primer Preparation)

The purified enzyme RDR obtained in Example 1 was denatured in the presence of 8 M urea and then digested with lysyl endopeptidase derived from *Achromobacter* (product of Wako Pure Chemical Industries, Ltd.). The amino acid sequences of the resulting peptide fragments were determined using a model ABI 492 protein sequencer (product of PerkinElmer). Based on these amino acid sequences, two DNA primers (primer 1, SEQ ID NO:3; primer 2, SEQ ID NO:4) were synthesized in the conventional manner.

(RDR Gene Amplification by PCR)

Chromosomal DNA was extracted from cultured cells of *Devosia riboflavina* IFO 13584 by the method of Murray et al. (Nucl., Acids Res. 8: 4321-4325 (1980)). Then, using the DNA primers prepared as described above, PCR was carried out with the chromosomal DNA obtained as a template. A DNA fragment, about 700 bp in size and supposed to be part of the RDR gene, was amplified (PCR was carried out using TaKaRa Ex Taq (product of Takara Shuzo Co., Ltd.) as DNA polymerase under the reaction conditions described in the manual attached thereto). This DNA fragment was cloned in the plasmid pT7Blue T-Vector (product of Novagen), and the base sequence thereof was confirmed using the ABI PRISM Dye Terminator Cycle Sequencing Ready Reaction Kit (product of PerkinElmer) and the ABI 373A DNA Sequencer (product of PerkinElmer).

(Full-Length Sequence Determination of the RDR Gene by i-PCR)

The chromosomal DNA of *Devosia riboflavina* IFO 13584 was completely digested with the restriction enzyme EcoRI, and the DNA fragment mixture obtained was subjected to intramolecular cyclization using T4 ligase. Using the cyclization product as a template, the full-length base sequence of the RDR gene on the chromosomal DNA was determined by the i-PCR technique (Nucl. Acids Res., 16, 8186 (1988)) based on the partial base sequence information about the RDR gene as revealed in the above paragraph (PCR was carried out using TaKaRa Ex Taq (product of Takara Shuzo Co., Ltd.) as a DNA polymerase, under the conditions described in the manual attached thereto. The base sequence determination was made as described hereinabove.).

The base sequence determined is shown in FIG. 1. The amino acid sequence encoded by the base sequence is shown below the base sequence. Comparison of this amino acid sequence with the partial amino acid sequences of the lysyl endopeptidase-digested fragments of the purified RDR revealed that the partial amino acid sequences of the purified RDR were all found in this amino acid sequence. The underlined portions in the amino acid sequence shown in FIG. 1 are the portions matching with the partial amino acid sequences of the purified RDR. The base sequence and amino acid sequence shown in FIG. 1 are the same as those shown under SEQ ID NO:2 in the sequence listing.

EXAMPLE 4

Construction of an RDR Gene-containing Recombinant Plasmid

Based on the base sequence determined in Example 3, an N-terminal DNA primer (primer 3, SEQ ID NO:5) resulting from addition of an NdeI site to the initiation codon moiety of the RDR gene and a C-terminal DNA primer (primer 4, SEQ ID NO:6) resulting from addition of an EcoRI site to just behind the 3' terminus of the same gene were synthesized. Then, PCR was carried out using the two DNAs as primers, and the chromosomal DNA of *Devosia riboflavina* IFO 13584 prepared in Example 3 as a template, the RDR gene with an NdeI site added to the initiation codon moiety and an EcoRI cleavage site added just behind the 3' terminus was amplified (PCR was carried out using Takara Ex Taq (product of Takara Shuzo Co., Ltd.) as a DNA polymerase under the reaction conditions described in the manual attached thereto.). This was digested with NdeI and EcoRI, and the resulting fragment was inserted into the plasmid pUCNT (WO 94/03613) at the NdeI-EcoRI site downstream from the lac promoter to obtain a recombinant plasmid pNTDR.

EXAMPLE 5

Construction of a Recombinant Plasmid Containing both the RDR Gene and the Glucose dehydrogenase Gene Based on the base sequence information about the glucose dehydrogenase derived from *Bacillus megaterium* IAM 1030 (hereinafter referred to as "GDH") gene (Eur. J. Biochem. 186,389 (1989)), an N-terminal DNA primer (primer 5, SEQ ID NO:7) resulting from addition of the Shine-Dalgarno sequence derived from *Escherichia coli* (9 bases) at 5 bases upstream of the initiation codon of the structural gene for GDH and further addition of an EcoRI cleavage site just before that sequence and a C-terminal DNA primer (primer 6, SEQ ID NO:8) resulting from addition of a SalI site just behind the termination codon of the structural gene for GDH were synthesized in the conventional manner. Using these two DNA primers and using the plasmid pGDK1 (Eur. J. Biochem., 186, 389 (1989)) as a template, a double-stranded DNA was synthesized by PCR. The DNA fragment was digested with EcoRI and SalI, and the digest was inserted into the EcoRI-SalI site downstream from the lac promoter of the plasmid pUCNT (WO 94/03613), a recombinant plasmid pNTG1 was obtained. Next, the RDR gene obtained by digesting pNTDR prepared in Example 4 with NdeI and EcoRI was inserted into the NdeI-EcoRI site located on the upstream of GDH gene on this pNTG1 to obtain a plasmid pNTDRG1. The construction scheme for and the structure of pNTDRG1 are shown in FIG. 2.

EXAMPLE 6

Recombinant *Escherichia coli* Production

The recombinant plasmids PNTDR and pNTDRG1 obtained in Examples 4 and 5 were used to transform *Escherichia coli* HB101 (product of Takara Shuzo Co., Ltd.) to obtain transformant *Escherichia coli* strains HB101(pNTDR) and HB101(pNTDRG1), respectively.

The thus-obtained transformants *Escherichia coli* HB101 (pNTDR) and HB101(pNTDRG1) have been deposited, as of Aug. 25, 2003, with the National Institute of Advanced Industrial Science and Technology International Patent Organism Depositary, Central 6, 1-1-1 Higashi, Tsukuba, Ibaraki, Japan, under the accession numbers FERM BP-08457 and FERM BP-08458, respectively.

EXAMPLE 7

RDR production in Recombinant *Escherichia coli* species

The recombinant *Escherichia coli* strain HB101(pNTDR) obtained in Example 6 was cultivated in 2×YT medium containing 120 μg/ml of ampicillin. Cells were collected by centrifugation and then suspended in 100 mM phosphate buffer (pH 6.5) and disrupted using a model UH-50 ultrasonic homogenizer (product of SMT Co., Ltd.) to obtain a cell-free extract.

The RDR activity of this cell-free extract was determined in the following manner. The RDR activity was determined by adding the substrate N-benzyl-3-pyrrolidinone (5 mM), the coenzyme NADH (0.25 mM) and the enzyme to 100 mM phosphate buffer (pH 6.5), and measuring the decrease in absorbance at a wavelength of 340 nm at 30° C. The enzyme activity oxidizing 1 μmol of NADH to NAD per minute under these reaction conditions was defined as 1 unit. The thus-measured RDR activity in the cell-free extract was expressed in terms of specific activity and compared with that of the vector plasmid-harboring transformant. Similarly, the RDR activity in the cell-free extract from *Devosia riboflavina* IFO 13584 as prepared in the same manner as in Example 1 was determined for comparison. The results of those determinations are shown in Table 1.

A distinct increase in RDR activity was observed in *Escherichia coli* HB101 (pNTDR) as compared with *Escherichia coli* HB101 (pUCNT) harboring the vector plasmid alone, and the specific activity was about 17 times higher as compared with *Devosia riboflavina* IFO 13584.

TABLE 1

| Microbial strain | RDR specific activity (U/mg) |
| --- | --- |
| E. coli HB101 (pUCNT) | <0.01 |
| E. coli HB101 (pNTDR) | 0.67 |
| Devodia riboflavina IF013584 | 0.04 |

EXAMPLE 8

Simultaneous Expression of RDR and GDH in Recombinant *Escherichia coli* Strains The recombinant *Escherichia coli* strain HB101(pNTDRG1) obtained in Example 6 was treated in the same manner as in Example 7, and the cell-free extract obtained was assayed for GDH activity in the following manner. The GDH activity was measured by adding the substrate glucose (0.1 M), the coenzyme NADP (2 mM) and the enzyme to 1 M Tris-hydrochloride buffer (pH 8.0) and measuring the increase in absorbance at a wavelength of 340 nm at 25° C. The enzyme activity reducing 1 μmol of NADP to NADPH per minute under these reaction conditions was defined as 1 unit. The RDR activity was also measured in the same manner as in Example 7.

The thus-measured RDR and GDH activities of the cell-free extract were each expressed in terms of specific activity and compared with the results with *Escherichia coli* HB101 (pNTDR) and the transformant HB101(pUCNT) harboring the vector alone. The comparative results are shown in Table 2. With *Escherichia coli* HB101(pNTDRG1), distinct increases in RDR activity and GDH activity were found as compared with the transformant *Escherichia coli* HB101 (pUCNT) harboring the vector plasmid alone.

TABLE 2

| Microbial strain | RDR specific activity (U/mg) | GDH specific activity (U/mg) |
| --- | --- | --- |
| E. coli HB101 (pUCNT) | <0.01 | <0.01 |
| E. coli HB101 (pNTDR) | 0.67 | <0.01 |
| E. coli HB101 (pNTDRG1) | 0.47 | 111 |

EXAMPLE 9

Synthesis of (R)-N-benzyl-3-pyrrolidinol from N-benzyl-3-pyrrolidinone Using the Recombinant *Escherichia coli* Strain for Simultaneous Expression of RDR and Glucose Dehydrogenase The culture of the recombinant *Escherichia coli* HB101 (pNTDRG1) as obtained in Example 8 was subjected to ultrasonic cell disruption using SONIFIRE 250 (product of BRANSON). To 20 ml of this cell disruption fluid, there were added 2 g of glucose, 1 mg of NAD and 1 g of N-benzyl-3-pyrrolidinone. This reaction mixture was stirred at 30° C. for 18 hours under a nitrogen atmosphere while adjusting the pH to 6.5 by adding 5 M hydrochloric acid and sodium hydroxide solution. After completion of the reaction, 2 ml of 5 M sodium hydroxide solution was added, and this reaction mixture was extracted with toluene. The solvent was then removed from the extract by an evaporator, and the extract was analyzed. Then, N-benzyl-3-pyrrolidinol was obtained in 96% yield. The N-benzyl-3-pyrrolidinol formed on that occasion was the R form with an optical purity of 99.9% ee.

The quantitation of N-benzyl-3-pyrrolidinone and N-benzyl-3-pyrrolidinol was carried out by gas chromatography (column: GL Sciences Inc.'s UniportB 10% PEG-20 M (ID 3.0 mm×1.0 m), column temperature: 200° C., career gas: nitrogen, detection: FID)).

The determination of the optical purity of N-benzyl-3-pyrrolidinol was carried out by high-performance liquid column chromatography (column: Daicel Chemical Industries' Chiralcel OB (ID 4.6 mm×250 mm), eluent: n-hexane/isopropanol/diethyl amine=99/1/0.1, flow rate: 1 ml/min, detection: 254 nm, column temperature: room temperature).

EXAMPLE 10

Synthesis of (R)-7-methoxy-2-tetralol from 7-methoxy-2-tetralone Using the Recombinant *Escherichia coli* Strain for Simultaneous Expression of RDR and Glucose Dehydrogenase To 20 ml of the culture of the recombinant *Escherichia coli* HB101(pNTDRG1) as obtained in Example 8, 3 g of glucose, 2 mg of NAD and 2 g of 7-methoxy-2-tetralone were added. While adjusting the pH to 6.5 by dropwise addition of 5 M sodium hydroxide solution, the mixture was stirred at 30° C. for 15 hours under a nitrogen atmosphere. This reaction mixture was extracted with toluene, the solvent was then removed, and the extract was applied to silica gel column chromatography to obtain 1.7 g of 7-methoxy-2-tetralol. As a result of the optical purity determination, 7-methoxy-2-tetralol thus generated was the R form with an optical purity of 99.9% ee. $^1$H-NMR (CDCl$_3$), δppm 1.62 (s, 1H), 1.73-1.87

(m, 1H), 1.98-2.08 (m, 1H), 2.70-2.81 (m, 2H), 2.88 (app dt, 1H), 3.05 (dd, 1H), 3.76 (s, 3H), 4.09-4.19 (m, 1H), 6.61 (d, 1H), 6.69 (dd, 1H), 7.00 (d, 1H)

The quantitation of 7-methoxy-2-tetralone and 7-methoxy-2-tetralol was carried out by high-performance liquid column chromatography (column: Nacalai Tesque's COSMOSIL 5C8-MS (ID 4.6 mm×250 mm), eluent: water/acetonitrile=1/1, flow rate: 1 ml/min, detection; 210 nm, column temperature: room temperature).

The optical purity of 7-methoxy-2-tetralol was determined by high-performance liquid column chromatography (column: Daicel Chemical Industries' Chiralcel OJ (ID 4.6 mm×250 mm), eluent: n-hexane/isopropanol=9/1, flow rate: 1 ml/min, detection: 254 nm, column temperature: room temperature).

EXAMPLE 11

Synthesis of (R)-3-methoxy-6,7,8,9-tetrahydro-5H-benzocycloheptene-6-ol from 3-methoxy-6,7,8, 9-tetrahydro-5H-benzocycloheptene-6-one Using the Recombinant *Escherichia coli* Strain for Simultaneous Expression of RDR and Glucose Dehydrogenase To 20 ml of the culture of the recombinant *Escherichia coli* HB101(pNTDRG1) as obtained in Example 8, 3 g of glucose, 2 mg of NAD and 4 g of 50% (w/w) 3-methoxy-6, 7,8,9-tetrahydro-5H-benzocycloheptene-6-one in toluene were added. While adjusting the pH to 6.5 by dropwise addition of 5 M sodium hydroxide solution, the mixture was stirred at 30° C. for 18 hours under a nitrogen atmosphere. This reaction mixture was extracted with toluene, the solvent was then removed, and the extract was applied to silica gel column chromatography to obtain 1.6 g of 3-methoxy-6,7,8,9-tetrahydro-5H-benzocycloheptene-6-ol. As a result of the optical purity determination, 3-methoxy-6,7,8,9-tetrahydro-5H-benzocycloheptene-6-ol thus generated was the R form with an optical purity of 99.9% ee.

$^1$H-NMR (CDCl$_3$) δppm 1.40-1.65 (m, 2H), 1.70-1.95 (m, 2H), 1.95-2.20 (m, 1H), 2.65-2.75 (m, 2H), 2.90-3.10 (m, 2H), 3.78 (s, 3H), 3.65-3.90 (m, 1H), 6.66 (dd, 1H), 6.73 (d, 1H), 6.98 (d, 1H)

The quantitation of 3-methoxy-6,7,8,9-tetrahydro-5H-benzocycloheptene-6-one and 3-methoxy-6,7,8,9-tetrahydro-5H-benzocycloheptene-6-ol was carried out by high-performance liquid column chromatography (column: Nacalai Tesque's COSMOSIL 5C8-MS (ID 4.6 mm×250 mm), eluent: water/acetonitrile=1/1, flow rate: 1 ml/min, detection; 210 nm, column temperature: room temperature).

The optical purity of 3-methoxy-6,7,8,9-tetrahydro-5H-benzocycloheptene-6-ol was determined by high-performance liquid column chromatography (column: Daicel Chemical Industries' Chiralcel OJ (ID 4.6 mm×250 mm), eluent: n-hexane/isopropanol=9/1, flow rate: 1 ml/min, detection: 254 nm, column temperature: room temperature).

EXAMPLE 12

Synthesis of (S)-2-chloro-1-(4'-fluorophenyl)ethanol from 2-chloro-1-(4'-fluorophenyl)ethanone Using the Recombinant *Escherichia coli* Strain for Simultaneous Expression of RDR and Glucose Dehydrogenase To 50 ml of the culture of the recombinant *Escherichia coli* HB101(pNTDRG1) as obtained in Example 8, 10 g of glucose, 5 mg of NAD and 10 g of 50% (w/w) 2-chloro-1-(4'-fluorophenyl)ethanone in toluene were added. While adjusting the pH to 6.5 by dropwise addition of 5 M sodium hydroxide solution, the mixture was stirred at 30° C. for 22 hours. This reaction mixture was extracted with toluene, the solvent was then removed, and distilled (110° C., 0.8 mmHg) to obtain 4.1 g of 2-chloro-1-(4'-fluorophenyl)ethanol as a colorless oil. As a result of the optical purity determination, 2-chloro-1-(4'-fluorophenyl)ethanol thus generated was the S form with an optical purity of 99.9% ee.

$^1$H-NMR (CDCl$_3$) δppm 3.10 (s, 1H), 3.61 (dd, 1H), 3.70 (dd, 1H), 4.88 (dd, 1H), 7.06 (m, 2H), and 7.35 (m, 2H)

The quantitation of 2-chloro-1-(4'-fluorophenyl)ethanone and 2-chloro-1-(4'-fluorophenyl)ethanol was carried out by high-performance liquid column chromatography (column: YMC Co., Ltd.'s YMC-Pack ODS A-303 (ID 4.6 mm×250 mm), eluent: water/acetonitrile=1/1, flow rate: 1 ml/min, detection; 210 nm, column temperature: room temperature).

The optical purity of 2-chloro-1-(4'-fluorophenyl)ethanol was determined by high-performance liquid column chromatography (column: Daicel Chemical Industries' Chiralcel OJ (ID 4.6 mm×250 mm), eluent: n-hexane/isopropanol=39/1, flow rate: 1 ml/min, detection: 254 nm, column temperature: room temperature).

EXAMPLE 13

Synthesis of (S)-2-chloro-1-(3'-chlorophenyl)ethanol from 2-chloro-1-(3'-chlorophenyl)ethanone Using the Recombinant *Escherichia coli* Strain for Simultaneous Expression of RDR and Glucose Dehydrogenase To 50 ml of the culture of the recombinant *Escherichia coli* HB101(pNTDRG1) as obtained in Example 8, 10 g of glucose, 5 mg of NAD and 10 g of 50% (w/w) 2-chloro-1-(3'-chlorophenyl)ethanone in toluene were added. While adjusting the pH to 6.5 by dropwise addition of 5 M sodium hydroxide solution, the mixture was stirred at 30° C. for 22 hours. This reaction mixture was extracted with toluene, the solvent was then removed, and the extract was analyzed. As a result, 2-chloro-1-(3'-chlorophenyl)ethanol was obtained in 97% yield. The 2-chloro-1-(3'-chlorophenyl)ethanol formed on that occasion was the S form with an optical purity of 99.9% ee.

The quantitation of 2-chloro-1-(3'-chlorophenyl)ethanone and 2-chloro-1-(3'-chlorophenyl)ethanol was carried out in the same manner as in the cases of 2-chloro-1-(4'-fluorophenyl)ethanone and 2-chloro-1-(4'-fluorophenyl)ethanol. In addition, the optical purity of 2-chloro-1-(3'-chlorophenyl)ethanol was carried out in the same manner as in the case of 2-chloro-1-(4'-fluorophenyl)ethanol.

EXAMPLE 14

Substrate Specificity of RDR

In 100 mM phosphate buffer (pH 6.5) containing 0.33% (v/v) of dimethyl sulfoxide, various carbonyl compounds to be substrates shown in Table 3 and coenzyme NADH were dissolved to final concentrations of 1 mM and 0.25 mM, respectively. RDR was added thereto, and the decrease in absorbance at a wavelength of 340 nm at 30° C. was measured. The enzyme activity oxidizing 1 μmol of NADH to NAD per minute under these reaction conditions was defined as 1 unit. The activities to various carbonyl compounds were expressed in terms of relative values with the activity to N-benzyl-3-pyrrolidinone being taken as 100%, and shown in Table 3. RDR showed reduction activity to significantly wide range of carbonyl compounds.

TABLE 3

Substrate specificity of the reductase RDR

| Reaction substrate | % activity |
| --- | --- |
| N-benzyl-3-pyrrolidinone | 100 |
| 2-acetylpyridine | 13 |
| 3-acetylpyridine | 788 |
| 4-acetylpyridine | 6448 |
| 2-acetylpyrrole | 70 |
| acetophenone | 181 |
| m-hydroxyacetophenone | 61 |
| m-nitroacetophenone | 6927 |
| p-chloroacetophenone | 2354 |
| 4-fluoroacetophenone | 366 |
| 3,4-dimethoxyacetophenone | 2073 |
| p-methylacetophenone | 521 |
| 2-hydroxyacetophenone | 30 |
| 2-chloro-1-(3'-chlorophenyl)ethanone | 463 |
| 1-phenyl-2-butanone | 147 |
| propiophenone | 27 |
| benzoin | 13 |
| benzylacetone | 410 |
| acetone | 194 |
| 2-butanone | 280 |
| 2-hexanone | 5043 |
| 2-heptanone | 2777 |
| diethyl ketone | 32 |
| chloroacetone | 4170 |
| hydroxyacetone | 100 |
| 4-hydroxy-2-butanone | 33 |
| diacetyl | 1614 |
| acetylacetone | 1354 |
| 4-methyl-2-pentanone | 962 |
| cyclopropyl methyl ketone | 20 |
| cyclopentanone | 103 |
| dihydro-4,4-dimethyl-2,3-furandione | 1314 |
| ethyl 3-oxocyclopentane carboxylate | 87 |
| methyl pyruvate | 1889 |
| ethyl pyruvate | 6232 |
| methyl acetoacetate | 8341 |
| ethyl acetoacetate | 4236 |
| tert-butyl acetoacetate | 5634 |
| ethyl 2-methylacetoacetate | 239 |
| ethyl 2-chloroacetoacetate | 8907 |
| ethyl 2-eteneacetoacetate | 429 |
| ethyl 2-oxodecanoate | 18 |
| ethyl 4-chloroacetoacetate | 683 |
| n-octyl 4-chloroacetoacetate | 224 |

TABLE 3-continued

Substrate specificity of the reductase RDR

| Reaction substrate | % activity |
| --- | --- |
| ethyl 4-bromoacetoacetate | 4099 |
| ethyl 4-azideacetoacetate | 804 |
| ethyl 4-hydroxyacetoacetate | 1774 |
| ethyl 4-benzyloxyacetoacetate | 3186 |
| ethyl 4-acetoxyacetoacetate | 4234 |
| benzyl acetoacetate | 2015 |
| ethyl benzoylacetate | 98 |
| ethyl 2-chloro-3-oxo-3-phenyloropionate | 52 |
| benzaldehyde | 21 |
| 2-pyridinecarbaldehyde | 82 |
| pyridine-4-aldehyde | 441 |
| o-chlorobenzaldehyde | 9 |
| m-chlorobenzaldehyde | 301 |
| p-chlorobenzaldehyde | 117 |
| o-nitrobenzaldehyde | 33 |
| m-nitrobenzaldehyde | 683 |
| p-nitrobenzaldehyde | 1296 |
| propionaldehyde | 204 |
| n-butylaldehyde | 728 |
| n-hexylaldehyde | 2225 |
| 2-phenylpropionaldehyde | 706 |
| 3-phenylpropionaldehyde | 685 |
| methyl glyoxal | 345 |
| glutaraldehyde | 1339 |
| 7-methoxy-2-tetoralone | 7084 |
| 6-methoxy-2-tetoralone | 156 |
| 6,7-dimethoxy-2-tetoralone | 2267 |
| 2-tetoralone | 1721 |
| 2-keto-n-butyric acid | 15 |
| oxalacetic acid | 14 |
| levulinic acid | 11 |

INDUSTRIAL APPLICABILITY

As a result of gene cloning of a polypeptide gene having activity in stereoselectively reducing N-benzyl-3-pyrrolidinone to form (R)-N-benzyl-3-pyrrolidinol and analysis of the nucleotide sequence thereof, it has become possible to obtain a transformant highly capable of producing the polypeptide. It has also become possible to obtain a transformant capable of producing the polypeptide and glucose dehydrogenase simultaneously at high levels. Further, it has become possible to synthesize various optically active alcohols from the corresponding carbonyl compounds with good efficiency by using said transformant.

The invention claimed is:
1. An isolated polynucleotide which is the following (a), (b) or (c):
   (a) a polynucleotide comprising the nucleotide sequence of SEQ ID NO:2,
   (b) a polynucleotide capable of hybridizing with a polynucleotide comprising the nucleotide sequence fully complementary to the nucleotide sequence of SEQ ID NO:2 under stringent conditions, wherein said stringent conditions comprise washing a filter with 0.1 to 2×SSC solution at 65° C., and coding for a polypeptide having activity in stereoselectively reducing N-benzyl-3-pyrrolidinone represented by the formula (1):

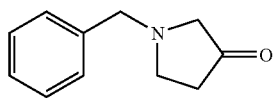
(1)

to form (R)-N-benzyl-3-pyrrolidinol represented by the formula (2):

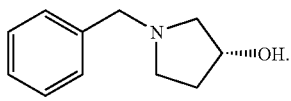
(2)

(c) a polynucleotide having at least 90% homology to the nucleotide sequence of SEQ ID NO:2, wherein said polynucleotide encodes a polypeptide with carbonyl reductase activity.
2. An expression vector which contains the polynucleotide according to claim 1.
3. The expression vector according to claim 2 which is a plasmid pNTDR.
4. The expression vector according to claim 2 which further contains a polynucleotide coding for a polypeptide having glucose dehydrogenase activity.
5. The expression vector according to claim 4, wherein the polypeptide having glucose dehydrogenase activity is a glucose dehydrogenase derived from *Bacillus megaterium*.
6. The expression vector according to claim 5 which is a plasmid pNTDRG1.
7. A transformant which is obtainable by transforming an isolated host cell using the expression vector according to claim 2.
8. The transformant according to claim 7, wherein the host cell is *Escherichia coli*.
9. The transformant according to claim 8 which is *E. coli* HB101(PNTDR) (FERM BP-08457).
10. The transformant according to claim 8 which is *E. coli* HB101(PNTDRG1) (FERM BP-08458).
11. A method for producing an optically active alcohol which comprises reacting the culture of the transformant according to claim 7 with a carbonyl group-containing compound, wherein the carbonyl group-containing compound is N-benzyl-3-pyrrolidinone represented by the formula (1):

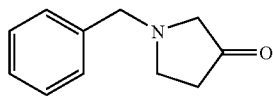
(1)

and the above optically active alcohol is (R)-N-benzyl-3-pyrrolidinol represented by the formula (2):

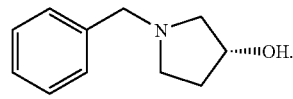
(2)

12. A method for producing an optically active alcohol which comprises reacting the culture of the transformant according to claim 7 with a carbonyl group-containing compound, wherein the carbonyl group-containing compound is a 2-tetralone derivative represented by the formula (3):

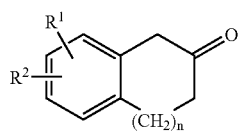
(3)

in the formula, R.sup.1 and R.sup.2 may be the same or different and each represents a hydrogen atom, a hydroxyl group or alkoxy group, and n represents 1 or 2, and
   the above optically active alcohol is a 2-tetralol derivative represented by the formula (4):

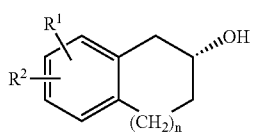
(4)

in the formula, R.sup.1, R.sup.2 and n are the same as defined above.
13. The method according to claim 12, wherein the above 2-tetralone derivative is 7-methoxy-2-tetralone, and the above 2-tetralol derivative is (R)-7-methoxy-2-tetralol.
14. The method according to claim 12, wherein the above 2-tetralone derivative is 3-methoxy-6,7,8,9-tetrahydro-5H-benzocycloheptene-6-One, and the above 2-tetralol derivative is (R)-3-methoxy-6,7,8,9-tetrahydro-5-H-benzocycloheptene-6-ol.
15. A method for producing an optically active alcohol which comprises reacting the culture of the transformant according to claim 7 with a carbonyl group-containing compound, wherein the above carbonyl group-containing compound is a 1-phenylethanone derivative represented by the general formula (5):

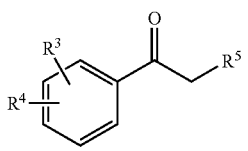
(5)

in the formula, R.sup.3 and R.sup.4 may be the same or different and each represents a hydrogen or halogen atom or an alkoxy or nitro group, R.sup.5 represents a hydrogen or halogen atom, a hydroxyl group or an alkyl group, which may optionally be substituted, and the above optically active alcohol is a 1-phenylethanol derivative represented by the general formula (6):

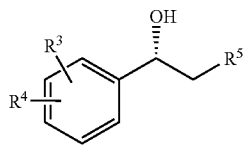
(6)

in the formula, R.sup.3, R.sup.4 and R.sup.5 are the same as defined above.

16. The method according to claim 15, wherein the above 1-phenylethanone derivative is 2-chloro-1-(4'-fluorophenyl)ethanone, and the above 1-phenylethanol derivative is (S)-2-chloro-1-(4'-fluorophenyl)ethanol.

17. The method according to claim 15, wherein the above 1-phenylethanone derivative is 2-chloro-1-(3'-chlorophenyl)ethanone, and the above 1-phenylethanol derivative is (S)-2-chloro-1-(3'-chlorophenyl)ethanol.

* * * * *

SEQUENCE LISTING

```
<160> NUMBER OF SEQ ID NOS: 2

<210> SEQ ID NO 1
<211> LENGTH: 250
<212> TYPE: PRT
<213> ORGANISM: Protein from Devosia riboflavina

<400> SEQUENCE: 1

Met Ser Gln Asp Phe Ser Gly Lys Val Ala Phe Val Thr Gly Gly Ala
1               5                   10                  15

Ser Gly Ile Gly Glu Ala Val Val Lys Gln Leu Ala Ala Arg Gly Ala
            20                  25                  30

Lys Val Val Val Ala Asp Leu Lys Leu Glu Gly Ala Gln Ala Val Ala
        35                  40                  45
```

```
Asp Ala Val Lys Ala Ala Gly Gly Glu Ala Ala Val Ala Val Asp
    50                  55                  60

Val Ala Lys Ala Asp Gln Val Glu Lys Ala Val Gln Phe Ala Val Asp
65                  70                  75                  80

Thr Phe Gly Ala Leu His Leu Ala Val Asn Asn Ala Gly Ile Gly Gly
                85                  90                  95

Ala Ser Ala Pro Leu Gly Asp Tyr Ser Phe Asp Trp His Arg Val
                100                 105                 110

Ile Asp Val Asn Leu Asn Ser Val Phe Tyr Ser Met Lys Tyr Glu Ile
                115                 120                 125

Val Ala Met Leu Arg Ala Gly Gly Ala Ile Val Asn Met Ala Ser
    130                 135                 140

Ile Leu Gly Ser Val Thr Phe Pro Asn Ala Pro Ala Tyr Val Thr Ala
145                 150                 155                 160

Lys His Gly Val Val Gly Met Thr Lys Ser Ala Ala Val Asp Tyr Ala
                165                 170                 175

Lys Lys Gly Ile Arg Val Thr Ala Val Gly Pro Gly Phe Ile Asp Thr
                180                 185                 190

Pro Leu Leu Ser Ala Leu Pro Lys Glu Thr Leu Asp Tyr Leu Lys Ser
                195                 200                 205

Val His Pro Ile Gly Arg Leu Gly Thr Ser Asp Glu Val Ala Ala Leu
    210                 215                 220

Thr Ala Phe Leu Leu Ser Asp Ala Ala Ser Asn Ile Thr Gly Ser Tyr
225                 230                 235                 240

His Leu Val Asp Gly Gly Tyr Val Ala Gln
                245                 250

<210> SEQ ID NO 2
<211> LENGTH: 753
<212> TYPE: DNA
<213> ORGANISM: Polynucleotide from Devosia riboflavina

<400> SEQUENCE: 2
atgtcccagg attttcagg caaggtcgca ttcgtaacgg gtggtgcctc gggcatcggt      60
gaggcggtcg tcaagcagct tgccgcgcgc ggcgccaagg ttgtggttgc cgatctcaag    120
ctcgaaggcg cgcaggcggt tgccgatgcc gtcaaggccg ccggcggcga agcggccgcg    180
gtagctgtcg atgtcgccaa gcccgatcag gtggagaagg ctgtccagtt cgccgtcgac    240
acctttggcg ccctgcatct ggcggtcaat aatgccggca ttggcggcgc ttccgctccc    300
ctcggcgatt attccttcga cgactggcat agggttatcg acgtcaatct caattccgtc    360
ttctattcga tgaagtacga gatcgtcgcc atgctcaggg caggcggtgg cgccatcgtc    420
aacatggcct ccatcctcgg ctcggtgacc tttcccaatg caccggccta tgtcaccgcc    480
aagcacggcg tggtcggcat gaccaagtcg gccgcggtgg actatgccaa aaagggcatt    540
cgcgtcacgg ccgtcgggcc cggtttcatc gacacgccgc tcctatccgc cttgccaag    600 gaaaccctgg actacctcaa atccgtccat ccgatcggac ggctgggtac ctcggatgaa    660
gtcgcagcgc tgaccgcgtt cctgctctcc gatgcagcgt cgaacatcac cggctcctat    720
cacctggtcg atggcggcta cgtcgcccaa tag                                 753
```